United States Patent [19]

Alwafaie

[11] Patent Number: 5,531,760
[45] Date of Patent: Jul. 2, 1996

[54] SKIN CLOSURE CLIP

[76] Inventor: Mohammed G. Alwafaie, P.O. Box 3854, Alkhobar 31952, Saudi Arabia

[21] Appl. No.: 421,862

[22] Filed: Apr. 14, 1995

[51] Int. Cl.$^6$ ................................................. A61B 17/04
[52] U.S. Cl. ............................................................. 606/216
[58] Field of Search ................................... 606/216, 213, 606/151

[56] References Cited

U.S. PATENT DOCUMENTS

| 2,472,009 | 5/1949 | Gardner | 606/216 |
| 3,586,002 | 6/1971 | Wood | 128/337 |
| 3,825,010 | 7/1974 | McDonald | 606/216 |
| 4,399,810 | 8/1983 | Samuels et al. | 128/337 |
| 4,815,466 | 3/1989 | Perlin | 128/325 |
| 4,997,439 | 3/1991 | Chen | 606/216 |
| 5,047,047 | 9/1991 | Yoon | 606/216 |
| 5,234,449 | 8/1993 | Bruker et al. | 606/158 |
| 5,236,440 | 8/1993 | Hlavacek | 606/216 |

Primary Examiner—Gary Jackson
Attorney, Agent, or Firm—Richard L. Miller

[57] ABSTRACT

The invention is a skin closure clip, for closing surrounding skin around a wound, comprising an elongated body. The body has two handle ends, and a lower surface and an upper surface between the handle ends. The upper surface has a downward curve and a middle. A pair of jaws extend downward from the lower surface. The body is flexed to bring the jaws apart. The jaws are brought into contact with the surrounding skin around the wound. The body is unflexed to bring the jaws together, closing the wound.

7 Claims, 1 Drawing Sheet

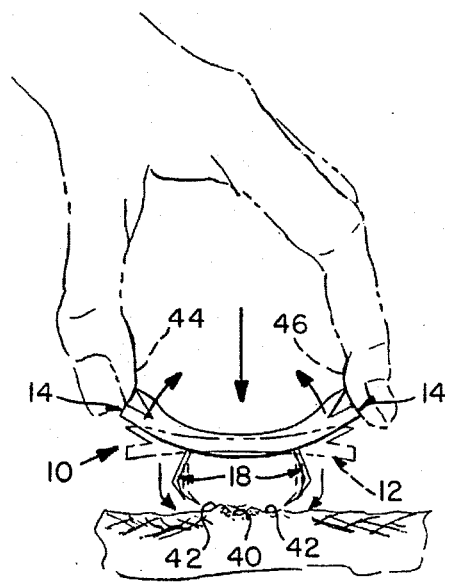
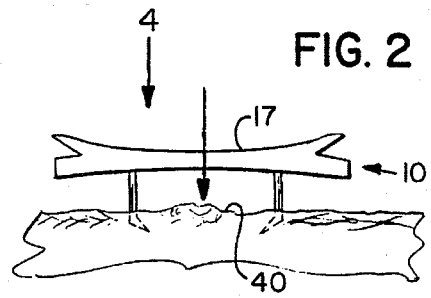
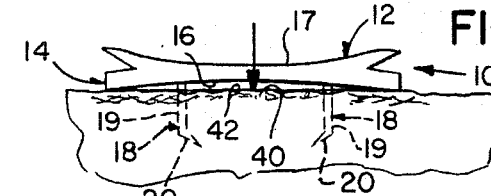
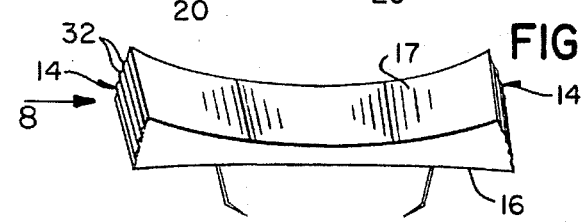
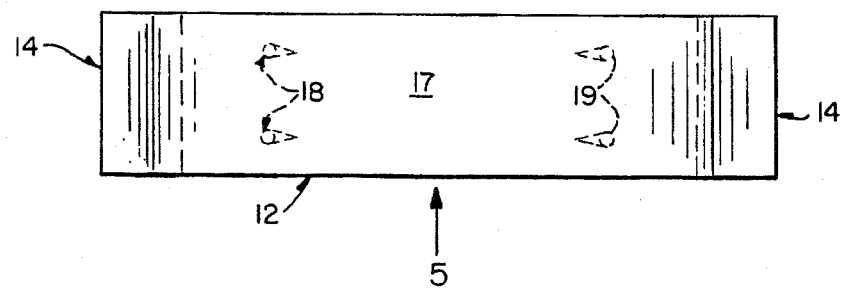
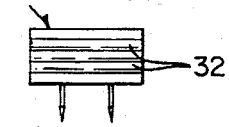
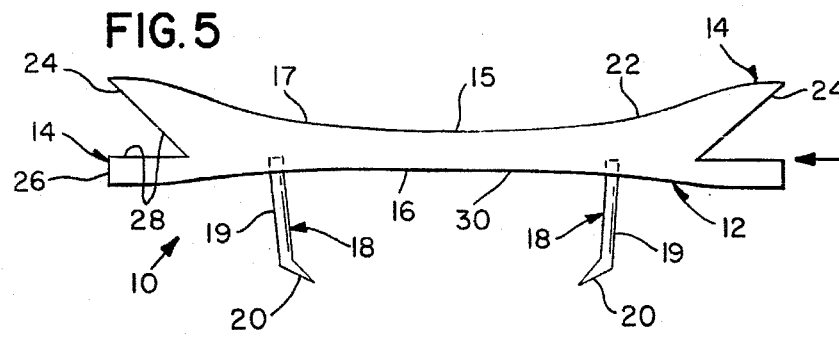
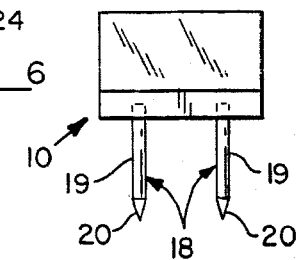

SKIN CLOSURE CLIP

BACKGROUND OF THE INVENTION

The invention relates to a skin closure clip. More particularly, the invention relates to a device for use in joining two sections of skin surrounding a wound or incision to allow proper healing.

When lacerations and incisions of the skin layer occur in wounds, surgical operations and the like, it has been the practice to stitch the separated portions of the skin together for the purpose of reducing scar formation and to accelerate healing. Such stitching operation constitutes a surgical operation wherein the separated sections of the skin are brought together and then stitched by needle and thread to hold the separated sections together until the wound has healed. When sufficient time has elapsed, such as three to six days, the stitches are removed by pulling the stitches from the wound after the thread has been severed.

This stitching operation constitutes a painful procedure which lasts over a considerable period of time. In addition, it requires the services of both hands of one or more physicians to hold the separated sections of the skin together, thread the needle, pass the needle through the adjacent edge sections of the skin layer, tie the thread with the desired tension to close the wound, and then to sever the loose ends of the thread when the stitch has been completed, all of which takes considerable time coupled with the interference of the bleeding wound.

The art has turned more recently to the use of metal clips which are applied by clip applicators which operate more or less in the fashion of a stapler to clip the free edges of the skin in a manner to hold the edges together until the wound has healed. The use of clips and clip applicators has materially reduced the time required to close a wound and has been effective to reduce the amount of effort and the amount of assistance required to effect skin closure. U.S. Pat. No. 4,399,810 to Samuels et al. discloses a skin clip that requires the use of a large stapler-like device to apply the clip.

U.S. Pat. No. 3,586,002 to Wood discloses a metal surgical skin clip.

U.S. Pat. No. 4,815,466 to Perlin discloses a surgical clip for temporarily occluding a blood vessel during surgery.

U.S. Pat. No. 5,234,449 to Bruker et al., discloses a surgical clip having a hinge, that is best suited for use after endoscopic surgery.

While these units may be suitable for the particular purpose employed, or for general use, they would not be as suitable for the purposes of the present invention as disclosed hereafter.

SUMMARY OF THE INVENTION

It is an object of the invention to produce a surgical clip that will effectively close a wound or incision with only minimal further intrusion into a patient s tissue.

It is another object of the invention to produce a surgical clip that may be manually operated, without the need for an additional application device to insert the clip.

It is a further object of the invention to produce a surgical clip that may be easily removed by a simple manual procedure once the wound or incision has healed, without producing further pain or trauma to the patient.

It is a still further object of the invention to provide a clip having a pair of hooked jaws, disposed along a flexible body, whose relative distance is altered as the body is flexed to grab skin surrounding a wound and then close the wound.

The invention is a skin closure clip, for closing surrounding skin around a wound, comprising an elongated body. The body has two handle ends, and a lower surface and an upper surface between the handle ends. The upper surface has a downward curve and a middle. A pair of jaws extend downward from the lower surface. The body is flexed to bring the jaws apart. The jaws are brought into contact with the surrounding skin around the wound. The body is unflexed to bring the jaws together, closing the wound.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

FIG. 1 is a diagrammatic elevational view illustrating the instant invention being inserted or removed from a wound.

FIG. 2 is a diagrammatic elevational view of an intermediate step of the invention being installed or removed from the wound.

FIG. 3 is a diagrammatic elevational view of the instant invention fully installed and closing the wound.

FIG. 4 is an enlarged top plan view taken in the direction of arrow 4 in FIG. 2 of the instant invention per se.

FIG. 5 is a side elevational view taken in the direction of arrow 5 in FIG. 4.

FIG. 6 is an end elevational view taken in the direction of arrow 6 in FIG. 5.

FIG. 7 is a diagrammatic view of a second embodiment of the instant invention.

FIG. 8 is an end elevational view taken in the direction of arrow 8 in FIG. 7.

DETAILED DESCRIPTION OF THE PREFERRED EMBODIMENTS

FIG. 5 illustrates a skin closure clip 10. The skin closure clip 10 has a body 12 which is elongated, substantially thin and is a flexible piece of inert material typically but not limited to elastomer or metal. The body 12 has two handle ends 14, and has a lower surface 16 and an upper surface 17, both extending between the handle ends 14. The body 12 has a middle section 15 having a cross-sectional area less than the cross-sectional area, midway between the handle ends 14. A pair of jaws 18 extend downwardly from the lower surface 16. Each of the jaws 18 are located near the handle ends 14. As the jaws 18 extend downward, they extend slightly toward each other, making a slight angle with each other. Each jaw 18 has a hook 20 opposite the lower surface 16. The hooks 20 on each jaw 18 are opposed to one another.

The body 12 has a downward curve 22 on the upper surface 17 between the handle ends 14, and is therefore concave between the handle ends 14. When pressure is applied to each of the handle ends 14, the natural tendency is for the body 12 to bend in a direction that further accentuates the downward curve 22 between the handle ends.

Each of the handle ends 14 may further have an upper handle 24 and a lower handle 26, separated by a handle notch 28. Thus, if pressure is exerted on the upper handles 24 of the handle ends 14, the middle 15 the body 12 will flex downward, forcing the jaws 18 and their hooks 20 away from each other, and creating a spring force in the body 12. As the pressure on the handle ends 14 is released, the body 12 springs back, unflexing and pulling the jaws 18 inward toward each other.

The lower surface 16 also may have an upward curve 30 between the handle ends 14. Further, the upward curve 30 can help accommodate contours in a patient s body.

FIG. 6 is a side view of the clip 10, illustrating that each of the jaws 18 may comprise two needles 19, each having its own hook 20. The use of two needles increases the pulling power of the jaws 18, while minimizing the intrusiveness of the jaws 18 or the clip 10 in general.

FIG. 4 is a top plan view, illustrating the relative positioning of the jaws 18, and the two needles 19 that each jaw comprises. Preferably, the dimensions of the body 12 in the plane of the top surface 17 are approximately 10–12 mm by 2–3 mm, with a thickness of approximately 1–2 mm. That is, the dimension between the handle ends 14 is approximately 10–12 mm. The distance between the jaws 18 will normally be about 7 to 8 mm. Further, the needles 19 should be thin: less than 25 gauge and preferably 28 gauge. The needles should have a length of approximately 2 to 3 mm from the lower surface 17.

FIG. 7 illustrates a second embodiment of the clip 10, in which the handle ends 14 have a plurality of horizontal ridges 32, to allow better gripping of the clip 10. The handle ends 14 are also tapered inwardly from the lower surface 16 to the upper surface 17.

FIG. 8 is a side view, illustrating the horizontal ridges 32 on one of the handle ends 14.

FIGS. 1, 2, and 3 illustrate the skin closure clip 10 in use to close a wound 40 surrounded by skin 42.

In FIG. 1, the clip 10 is held with a thumb 44 and forefinger 46 exerting pressure on the handle ends 14. The body 12 is flexed, forcing the jaws 18 apart. The jaws 18 are brought into contact with the skin 42, and the pressure upon the handle ends 14 is released. As the pressure is released, the spring force in the body 12 forces the jaws 18 toward each other.

In FIG. 2, the clip 10 has closed the wound 40, and now downward pressure is being exerted on the upper surface 17.

In FIG. 3, the clip 10 has been pushed fully downward, until the lower surface 16 is nearly flush with the skin 42. The clip 10 is now in a position to allow healing of the wound 40.

After the wound is given sufficient time to heal, the handle ends 14 are once again pressed upon to flex the body 12 and bring the jaws 18 apart. At the same time, the body 12 is pulled upward to remove the clip 10 from the wound 40.

Thus, in conclusion herein is presented a device for effectively closing a wound and allowing it to properly heal.

What is claimed is:

1. A skin closure clip, for closing a wound by grabbing skin surrounding the wound, comprising:

a) a body, the body being elongated and flexible, the body having a pair of handle ends, a middle with a cross section, and a lower surface extending between the pair of handle ends, each of the pair of handle ends having a top, bottom, a surface extending from the top to the bottom, and a cross section, the body further having an upper surface with a concave shape extending smoothly from substantially the top of one of the pair of handle ends to substantially the top of another of the pair of handle ends, the upper surface of the body having a middle that is midway between the pair of handle ends and is lower than the top of each of the pair of handle ends so as to provide the cross section area of the middle of the body to be less than the cross sectional area of each of the pair of handle ends; and b) a pair of jaws, the pair of jaws extending downward from the lower surface of the body, the pair of jaws having hooks for grabbing skin surrounding the wound, so that when compressive pressure is applied to each of the pair of handle ends the body flexes downwardly at the middle of the body due to the cross sectional area of the middle of the body being less than the cross sectional area of each of the pair of handle ends and therefore spreading the pair of jaws equally apart from the middle of the body.

2. The apparatus as recited in claim 1, wherein each of the jaws further comprises two needles, each having a hook.

3. The apparatus as recited in claim 2, wherein the lower surface further comprises an upward curve to help the body match skin contours.

4. The apparatus as recited in claim 3, wherein the top of each of the pair of handle ends is an upper handle, the bottom of each of the pair of handle ends is a bottom handle, and the surface extending from the top to the bottom is a notch, so that when the pressure is exerted on the upper handle of each of the pair of handle ends the middle of the body flexes downwardly forcing the jaws and the hooks of the jaws away from each other creating a spring force in the body and when the pressure on the upper handle of each of the pair of handle ends is released the body springs back unflexing and pulling the jaws inwardly toward each other.

5. The apparatus as recited in claim 3, wherein each of the pair of handle ends are tapered inwardly from the bottom to the top and includes a plurality of horizontal ridges so that better gripping by a user is provided during application of the clip.

6. The apparatus as recited in claim 1, wherein the distance between the handle ends is within the range of 10–12 mm.

7. The apparatus as recited in claim 6, wherein the needles are less than 25 gauge, and the jaws are substantially 7 mm apart.

\* \* \* \* \*